United States Patent [19]

Yoneda et al.

[11] Patent Number: 5,334,755
[45] Date of Patent: Aug. 2, 1994

[54] PROCESS FOR THE PRODUCTION OF ACETIC ACID FROM METHANOL AND CARBON MONOXIDE USING SUPPORTED RHODIUM CATALYST

[75] Inventors: Noriyuki Yoneda, Tokyo; Yoshimi Shiroto, Yokohama; Kazuhiko Hamato, Kawasaki; Sachio Asaoka, Yokohama; Tetsuo Maejima, Kiyose, all of Japan

[73] Assignee: Chiyoda Corporation, Japan

[21] Appl. No.: 49,303

[22] Filed: Apr. 21, 1993

[30] Foreign Application Priority Data

Apr. 24, 1992 [JP] Japan .................. 4-131790
Apr. 24, 1992 [JP] Japan .................. 4-131791

[51] Int. Cl.$^5$ .................. C07C 67/36; C07C 51/10
[52] U.S. Cl. .................. 562/519; 562/517; 562/607
[58] Field of Search .............. 562/519, 517, 406, 607, 562/608

[56] References Cited

U.S. PATENT DOCUMENTS

| | | | |
|---|---|---|---|
| 3,689,533 | 9/1972 | Schultz | 562/519 X |
| 3,717,670 | 2/1973 | Schultz | 562/519 X |
| 3,769,329 | 3/1973 | Paulik et al. | 260/488 |
| 3,855,307 | 12/1974 | Rony et al. | 562/519 X |
| 4,212,989 | 7/1980 | Isshiki et al. | 560/232 |
| 5,001,259 | 3/1991 | Smith et al. | 562/519 |
| 5,155,261 | 10/1992 | Marston et al. | 562/519 |
| 5,189,203 | 2/1993 | Hansen et al. | 562/519 X |

FOREIGN PATENT DOCUMENTS 1233121 5/1968 United Kingdom .

OTHER PUBLICATIONS

Applied Catalysts, 67(1991) 269–278, Hjortkjaer et al.

Primary Examiner—Arthur C. Prescott
Attorney, Agent, or Firm—Lorusso & Loud

[57] ABSTRACT

A liquid feed containing methanol, carbon monoxide, an alkyl iodide and a solvent is contacted with a supported rhodium catalyst to produce acetic acid at a temperature of 140°–250° C. and a pressure of 15–60 kg/cm$^2$G with a partial pressure of carbon monoxide of 7–30 kg/cm$^2$ while maintaining (a) the water concentration of the product solution in the range of 0.5–10% by weight and (b) the carbonylation degree $C_r$, defined in the specification, of the solution within the reactor at 0.15 or more. The solvent may be a carboxylic acid or a carboxylic acid ester.

8 Claims, 2 Drawing Sheets

PROCESS FOR THE PRODUCTION OF ACETIC ACID FROM METHANOL AND CARBON MONOXIDE USING SUPPORTED RHODIUM CATALYST

This invention relates to a process for the production of acetic acid by carbonylation of methanol.

One well known method of preparing acetic acid by carbonylation of methanol is Monsanto method in which methanol is reacted with carbon monoxide in an acetic acid solvent in which a rhodium compound and methyl iodide have been dissolved (British patent No. 1,233,121). This method has a problem because a large amount of acetic acid as solvent must be used in order to dissolve the rhodium compound catalyst and, hence, large-sized reactor and associated equipments must be used. This also causes an increase of operation costs. Another problem of the conventional method is that water should be present in the catalyst solution in a large amount in order to accelerate the carbonylation and to improve selectivity. A high water content is also desired for the prevention of precipitation of the catalyst. Such a large amount of water causes the hydrolysis of the methyl iodide used as a reaction accelerator to form a large amount of hydrogen iodide which causes corrosion of apparatuses and iodide contamination to the product, causing degradation of the quality of the product. The conventional method has also a problem because it requires the recovery and regeneration of the catalyst.

To cope with this problem, U.S. Pat. No. 5,155,261 proposes a method in which a solid catalyst including an insoluble, pyridine ring-containing resin and a rhodium compound supported on the resin is used. By adopting such a heterogeneous phase reaction, the above problems involved in the Monsanto method can be overcome. However, this method has a problem because the reaction should be performed at a temperature of 170°–200° C. and a carbon monoxide partial pressure of 65–80 Bar. With such a high partial pressure, the total reaction pressure becomes higher than 95 kg/cm$^2$G. This unavoidably causes an increase of apparatus costs and operation costs.

Continuous carbonylation of methanol in the presence of methyl iodide promoter using a flow type reactor having a fixed bed of a rhodium supporting polymer catalyst is shown in Hortkjaer et al, Applied Catalysis, 67, 269–278(1991). According to this report, however, the leaching out of rhodium considerably occurs so that, about several hours after the commencement of the reaction, the intrinsic activity is about 4.6 times lower than for the homogeneous catalyst.

The present invention has been made to overcome the above-mentioned problems of the known methanol carbonylation methods.

In accordance with the present invention there is provided a process for the production of acetic acid, comprising the steps of introducing a feed including methanol, carbon monoxide, an alkyl iodide and a solvent into a reaction zone containing a solid catalyst including an insoluble, pyridine-containing resin substrate, and a rhodium compound supported on said substrate; contacting said feed with said solid catalyst to react said methanol with said carbon monoxide and to obtain a reaction solution; and discharging at least a portion of said reaction solution from said reaction zone to obtain a product solution, characterized in that said solvent includes at least one organic solvent selected from the group consisting of carboxylic acids having at least two carbon atoms and carboxylic acid esters having at least two carbon atoms, and in that said reaction is performed at a temperature of 140°–250° C. and a pressure of 15–60 kg/cm$^2$G with a partial pressure of carbon monoxide of 7–30 kg/cm$^2$ while maintaining (a) the water concentration of said product solution in the range of 0.5–10% by weight and (b) the carbonylation degree $C_r$ of the solution within said reaction zone at 0.15 or more, wherein the carbonylation degree $C_r$ is given by the following equation:

$$C_r = (M[CH_3COOH] + M[CH_3COOCH_3] + M[CH_3COOR^1])/(M[CH_3COOH] + 2M[CH_3COOCH_3] + 2M[CH_3OCH_3] + M[CH_3COOR^1] + M[R^2COOCH_3] + M[CH_3OR^3] + M[CH_3OH])$$

wherein M[CH$_3$COOH], M[CH$_3$COOCH$_3$], M[CH$_3$COOR$^1$], M[CH$_3$OCH$_3$], M[R$^2$COOCH$_3$], M[CH$_3$OR$^3$] and M[CH$_3$OH] represent the amounts, in terms of molarity, of CH$_3$COOH, CH$_3$COOCH$_3$, CH$_3$COOR$^1$ where R$^1$ represents an alkyl group having at least two carbon atoms, CH$_3$OCH$_3$, R$^2$COOCH$_3$ where R$^2$ represents an alkyl group having at least two carbon atoms, CH$_3$OR$^3$ where R$^3$ represents an alkyl group having at least two carbon atoms and CH$_3$OH, respectively, which are present in the solution within said reaction zone.

In another aspect, the present invention provides a process for the production of acetic acid, comprising reacting, in a reaction zone, carbon monoxide with methanol in a solvent at a temperature of 140°–250° C. in the presence of an alkyl iodide and a solid catalyst including an insoluble, pyridine-containing resin substrate, and rhodium supported on said substrate, characterized in that said solvent includes an organic solvent selected from the group consisting of those having at least two carbonyl groups and mixtures thereof, that said reaction is performed at a pressure of 15–60 kg/cm$^2$G with a partial pressure of carbon monoxide of 7–30 kg/cm$^2$, and that the solution within said reaction zone contains said organic solvent in an amount of at least 0.30 part by weight per part by weight of the methanol contained therein.

By carrying out the methanol carbonylation in the manner described above, acetic acid can be obtained with both high yield and high selectivity even at a relatively low reaction pressure. Further, the catalytic activity can be maintained high for a long period of time.

The catalyst to be used in the present invention includes an insoluble, pyridine ring-containing polymer, and a rhodium compound supported thereon and is known per se. The term "pyridine ring-containing polymer" used herein is intended to refer to a polymer containing substituted or non-substituted pyridine rings or substituted or non-substituted, pyridine-containing polycondensed rings such as quinoline rings. The substituents include those inert to the methanol carbonylation such as an alkyl group and alkoxy group.

Typical examples of the insoluble, pyridine ring-containing polymers include those obtained by reaction of vinylpyridine with a divinyl monomer or by reaction of vinylpyridine with a divinyl monomer-containing vinyl monomer, such as copolymers of 4-vinylpyridine and divinylbenzene, copolymers of 2-vinylpyridine and divinylbenzene, copolymers of styrene, vinylbenzene and divinylbenzene, copolymers of vinylmethylpyridine and divinylbenzene and copolymers of vinylpyridine, methyl acrylate and ethyl diacrylate.

It is important that the above pyridine ring-containing polymer should be cross-linked by at least 10%, preferably 15-40%. A degree of cross-linking below 10% is disadvantageous because the polymer is apt to be swollen or shrunk upon contact with a solvent such as acetic acid so that the mechanical strengths of the catalyst become gradually poor during use. As the degree of cross-linking increases, the content of the pyridine rings is correspondingly reduced so that the amount of the rhodium compound supported on the catalyst is lowered. Thus, the degree of cross-linking is preferably not higher than 40% for reasons of high catalytic activity. The content of the pyridine ring in the catalyst is preferably 2.0-10 milliequivalents, more preferably 3.5-6.5 milli-equivalents, in terms of pyridine nitrogen per one gram of the catalyst. The term "degree of cross-linking" used herein is intended to refer to the content, in terms of % by weight, of the divinyl monomer.

The pyridine ring of the insoluble polymer may be in the free base or N-oxide form or quaternized form. The insoluble, pyridine ring-containing polymer is preferably in a bead form, more preferably in a spherical form, having a particle diameter of 0.01-2 mm, preferably 0.1-1 mm, more preferably 0.25-0.7 mm. Commercially available pyridine-containing polymers such as Reillex-425 (product of Reilly Tar and Chemical Corporation) and KEX-316, KEX-501 and KEX-212 (products of Koei Chemical Co., Ltd.) may be suitably used for the purpose of the present invention.

Any conventionally used method may be suitably adopted for loading a rhodium compound on the insoluble, pyridine-containing polymer. For example, by contacting the polymer with a solution containing an alkyl iodide and a rhodium salt under a pressure of carbon monoxide, the polymer is loaded with the rhodium salt. More convenient is a method in which the polymer is simply contacted with a reaction solution of methanol carbonylation containing a rhodium salt, methanol, an alkyl iodide and a solvent under a carbon monoxide pressure. It is considered that the rhodium salt, alkyl iodide and carbon monoxide are reacted with each other to form a rhodium carbonyl complex ($[RhI_2(CO)_2]^-$) which in turn is ionically bonded with a pyridinium salt obtained by quaternizing the pyridine ring of the polymer with the alkyl iodide.

Examples of the rhodium salts include rhodium halides such as rhodium chloride, rhodium bromide and rhodium iodide. As the alkyl group of the alkyl iodide, those having 1-6 carbon atoms are preferably used. Examples of alkyl iodides include methyl iodide, ethyl iodide and propyl iodide. The alkyl iodide promoter is generally used in an amount of 2-2,000 moles, more preferably 50-500 moles, per mole of the rhodium salt. The loading of the rhodium salt on the pyridine-containing polymer is generally performed at a carbon monoxide pressure of 7-30 kg/cm$^2$G, preferably 10-20 kg/cm$^2$G. The amount of rhodium compounds in the catalyst is generally 0.2-15% by weight, preferably 0.3-8% by weight, more preferably 0.1-1% by weight, based on the weight of the insoluble, pyridine-containing polymer.

The carbonylation of methanol using the above heterogeneous catalyst may be carried out using any desired reactor, such as a fixed bed reactor, an expansion bed reactor or a stirred tank reactor. The catalyst is placed in the reactor in an amount of, generally, 2-40% by weight based on the weight of the reaction solution contained therein, though the amount varies with the kind of the reactor used. It is recommendable to use the catalyst in an amount of 2-25% by weight in the case of a mixing type reactor, 20-40% by weight in the case of a fixed bed reactor and 2-25% by weight in the case of an expansion bed reactor, based on the reaction solution contained therein.

The process of the present invention includes a step of introducing a feed including methanol, carbon dioxide, an alkyl iodide and a solvent into a reactor containing the above solid catalyst. The feed is contacted with the solid catalyst to react the methanol with the carbon monoxide thereby to obtain a reaction solution. At least a portion of the reaction solution is discharged from the reactor as a product. The process is characterized in that the solvent includes at least one organic solvent selected from the group consisting of carboxylic acids having at least two carbon atoms and carboxylic acid esters having at least two carbon atoms, such as acetic acid and methyl acetate, and in that the reaction is performed at a temperature of 140°-250° C. and a pressure of 15-60 kg/cm$^2$G with a partial pressure of carbon monoxide of 7-30 kg/cm$^2$ while maintaining (a) the water concentration of the product solution in the range of 0.5-10% by weight and (b) the carbonylation degree $C_r$ of the solution within the reaction zone at 0.15 or more, wherein the carbonylation degree $C_r$ is given by the following equation:

$$C_r = (M[CH_3COOH] + M[CH_3COOCH_3] +$$

$$M[CH_3COOR^1])/(M[CH_3COOH] + 2M[CH_3COOCH_3] +$$

$$2M[CH_3OCH_3] + M[CH_3COOR^1] + M[R^2COOCH_3] +$$

$$M[CH_3OR^3] + M[CH_3OH])$$

wherein M[CH$_3$COOH], M[CH$_3$COOCH$_3$], M[CH$_3$COOR$^1$], M[CH$_3$OCH$_3$], M[R$^2$COOCH$_3$], M[CH$_3$OR$^3$] and M[CH$_3$OH] represent the amounts, in terms of molarity, of CH$_3$COOH, CH$_3$COOCH$_3$, CH$_3$COOR$^1$ where R$^1$ represents an alkyl group having at least two carbon atoms, CH$_3$OCH$_3$, R$^2$COOCH$_3$ where R$^2$ represents an alkyl group having at least two carbon atoms, CH$_3$OR$^3$ where R$^3$ represents an alkyl group having at least two carbon atoms and CH$_3$OH, respectively, which are present in the solution within the reaction zone. According to the above process, the installation costs, equipments costs and operation costs of the whole acetic acid production system can be significantly reduced.

More particularly, by performing the methanol carbonylation while maintaining the above conditions (a) and (b), the catalyst can exhibit a high catalytic activity and a high stability even when the carbon monoxide partial pressure is as low as 7 kg/cm$^2$. As described previously, the conventional carbonylation method using a heterogeneous, rhodium loaded catalyst as taught by U.S. Pat. No. 5,155,261 requires a partial pressure of carbon monoxide of 65-85 Bar. Thus, the fact that the carbonylation can be performed with a high yield and a high selectivity at a carbon monoxide partial pressure of 7-30 kg/cm$^2$ would be surprising.

In the present specification and appended claims, the following terms have the following meanings:

Water concentration $W_p$: the amount of water in terms of % by weight contained in the product discharged from the reactor. In the case of a batch-type reactor, for example, $W_p$ is equal to the amount of water contained in the reaction solution remaining in the reactor after the reaction. In the case of a piston flow-type or a continuous flow, stirred tank type reactor, $W_p$ is the amount of water contained in the product discharged from the reactor.

Carbonylation degree $C_r$: the value of the solution contained in the reactor given by the following equation:

$$C_r = (M[CH_3COOH] + M[CH_3COOCH_3] +$$
$$M[CH_3COOR^1])/(M[CH_3COOH] + 2M[CH_3COOCH_3] +$$
$$2M[CH_3OCH_3] + M[CH_3COOR^1] + M[R^2COOCH_3] +$$
$$M[CH_3OR^3] + M[CH_3OH])$$

wherein $M[CH_3COOH]$, $M[CH_3COOCH_3]$, $M[CH_3COOR^1]$, $M[CH_3OCH_3]$, $M[R^2COOCH_3]$, $M[CH_3OR^3]$ and $M[CH_3OH]$ represent the amounts, in terms of molarity, of $CH_3COOH$, $CH_3COOCH_3$, $CH_3COOR^1$ where $R^1$ represents an alkyl group having at least two carbon atoms, $CH_3OCH_3$, $R^2COOCH_3$ where $R^2$ represents an alkyl group having at least two carbon atoms, $CH_3OR^3$ where $R^3$ represents an alkyl group having at least two carbon atoms and $CH_3OH$, respectively, which are present in the solution within the reactor. The term "the solution within the reactor" used herein is intended to mean the solution which is present at any point in time in the course of the reaction (e.g. at the start of the reaction and at the end of the reaction). Since the amount of methanol decreases as the reaction proceeds, $C_r$ increases as the reaction proceeds. Thus, in the case of a batch-type reactor, for example, $C_r$ may be appropriately defined as the carbonylation degree of the whole raw material feed introduced into the reactor. In the case of a continuous flow, stirred tank-type reactor, since the solution in the reactor is homogeneously mixed, $C_r$ of the solution in the reactor is the same as the carbonylation degree of the solution discharged as product from the reactor. In the case of a piston flow-type reactor, since the reaction proceeds as the solution flows from the inlet to the outlet, $C_r$ may be appropriately defined as the carbonylation degree of the whole feed introduced into the reactor. In these cases, the feed includes not only fresh raw materials, such as methanol, solvent and alkyl iodide, but also any other liquid, such as unreacted methanol, dimethyl ether, methyl acetate, solvent and alkyl iodide, which are recycled from the succeeding steps such as an acetic acid separation step or from a cooler connected to the reactor for controlling the temperature of the reaction solution.

Water content $W_f$: the value of the feed given by the following equation:

$$W_f = (M[H_2O] - M[CH_3COOCH_3] - M[CH_3COOR^1] -$$
$$M[R^2COOCH_3] - M[CH_3OCH_3] - M[CH_3OR^3] -$$
$$M[R^4OR^5])/(M[CH_3COOH] + 2M[CH_3COOCH_3] +$$
$$2M[CH_3OCH_3] + M[CH_3COOR^1] + M[R^2COOCH_3] +$$
$$M[CH_3OR^3] + M[CH_3OH])$$

wherein $M[H_2O]$, $M[CH_3COOCH_3]$, $M[CH_3COOR^1]$, $M[R^2COOCH_3]$, $M[CH_3OCH_3]$, $M[CH_3OR^3]$, $M[R^4OR^5]$) and $M[CH_3OH]$ represent the amounts, in terms of molarity, of $H_2O$, $CH_3COOCH_3$, $CH_3COOR^1$, $R^2COOCH_3$, $CH_3OCH_3$, $CH_3OR^3$, $R^4OR^5$ and $CH_3OH$, respectively, contained in the feed. In the case of a batch-type reactor, for example, $W_f$ is the water content of the whole raw material feed introduced into the reactor. In the case of a continuous flow, stirred tank-type reactor or a piston flow-type reactor, $W_f$ is the water content of the whole feed introduced into the reactor. The feed includes not only fresh raw materials, such as methanol, carbon monoxide, solvent and alkyl iodide, but also any other liquid, such as unreacted methanol, dimethyl ether, methyl acetate, solvent and alkyl iodide, recycled from the succeeding steps such as an acetic acid separation step or from a cooler connected to the reactor for controlling the temperature of the reaction solution.

Carbonylation degree $C_p$: the value of the product solution given by the following equation:

$$C_p = (M[CH_3COOH] + M[CH_3COOCH_3] +$$
$$M[CH_3COOR^1])/(M[CH_3COOH] +$$
$$2M[CH_3COOCH_3] + 2M[CH_3OCH_3] +$$
$$M[CH_3COOR^1] + M[R^2COOCH_3] + M[CH_3OR^3] +$$
$$M[CH_3OH])$$

wherein $M[CH_3COOH]$, $M[CH_3COOCH_3]$, $M[CH_3COOR^1]$, $M[CH_3OCH_3]$, $M[R^2COOCH_3]$, $M[CH_3OR^3]$ and $M[CH_3OH]$ represent the amounts, in terms of molarity, of $CH_3COOH$, $CH_3COOCH_3$, $CH_3COOR^1$ where $R^1$ represents an alkyl group having at least two carbon atoms, $CH_3OCH_3$, $R^2COOCH_3$ where $R^2$ represents an alkyl group having at least two carbon atoms, $CH_3OR^3$ where $R^3$ represents an alkyl group having at least two carbon atoms and $CH_3OH$, respectively, which are present in the product solution. In the case of a batch-type reactor, for example, $C_p$ is a carbonylation degree of the reaction solution remaining in the reactor after the completion of the reaction. In the case of a piston flow-type or a continuous flow, stirred tank-type reactor, $C_p$ is the carbonylation degree of the product discharged from the reactor. $C_p$ is equal to or greater than $C_r$.

Rhodium concentration $Rh_r$: the amount of rhodium compound (as elemental rhodium) contained in the reactor based on the weight of the solution within the reactor.

It is important that the water concentration $W_p$ in the product should be maintained in the range of 0.5–10% by weight, in order to prevent the dissociation of the rhodium species from the pyridine-containing polymer and to maintain the catalytic activity in a high level. It has been unexpectedly found that when the carbonylation is performed while maintaining the water concentration in the product at 0.5% by weight or more, the carbonylation rate does not decrease even at a high methanol conversion, namely even when the carbonylation degree of about 1 is reached. Too high a water concentration $W_p$ in excess of 10% by weight is, however, disadvantageous because the costs for the separation of water from acetic acid are increased and because the rhodium species tend to be dissociated from the polymer substrate and exhausted from the reactor together with the product. This requires the separation of the rhodium species from acetic acid, which incurs much costs. Especially good results are obtainable with $W_p$ of 1–5% by weight and this range is preferred.

The carbonylation degree $C_r$ has also an influence upon the stability and activity of the catalyst. A value of $C_r$ of lower than 0.15 is disadvantageous because the methanol carbonylation rate is low and because the dissociation of the rhodium species from the catalyst is accelerated. The $C_r$ is preferably 0.55 or more, more preferably 0.7 or more.

It is preferred that the following conditions (c) and (d) be met:

(c) the carbonylation degree $C_p$ of the product discharged from the reactor is at least 0.80, more preferably at least 0.9; and (d) the water content $W_f$ of the feed introduced to the reactor is 0.30 or less, more preferably 0.20 or less.

The conversion of methanol increases with an increase of the carbonylation degree $C_p$ of the product. At the same time, the yield of by-products such as water, methyl acetate and dimethyl ether is reduced. Generally, the conversion of above 90% is reached when $C_p$ is 0.8 or more.

In the methanol carbonylation process, the main reaction (1) is accompanied with the side reactions (2) and (3):

$$CH_3OH + CO \rightleftharpoons CH_3COOH \quad (1)$$

$$CH_3COOH + CH_3OH \rightleftharpoons CH_3COOCH_3 + H_2O \quad (2)$$

$$2CH_3OH \rightleftharpoons CH_3OCH_3 + H_2O \quad (3)$$

Water is produced as a result of the side reactions (2) and (3). Since such water can hydrolyze alkyl iodide to form highly corrosive hydrogen iodide, it is desired that the yield of such water be sufficiently low. It has been found that when the above conditions (c) and (d) are satisfied, the occurrence of the side reactions is effectively prevented so that the water concentration $W_p$ of the product can be maintained at 5% by weight or less. This affords the following merits:

(i) hydrolysis the of alkyl iodide resulting in the formation of corrosive hydrogen iodide can be minimized;

(ii) separation of water from the acetic acid product is facilitated; and (iii) dissociation of rhodium species from the solid resin is minimized.

It is preferred that the solution within the reactor have a content of carbonyl group-containing compounds having at least two carbon atoms of at least 0.30 part by weight per part by weight of the methanol present in the solution within the reactor. Such carbonyl group containing compounds are used as a solvent and may be, for example, saturated aliphatic acids such as acetic acid, propionic acid and butyric acid, esters such as methyl acetate and ethyl acetate, aromatic acids such as benzoic acid, and mixtures thereof. By using such an organic solvent in such a specific amount, the catalyst can exhibit high catalytic activity and the dissociation of rhodium species from the polymer substrate can be minimized, so that the reaction can be performed at a low carbon monoxide partial pressure. Especially good results are obtainable with the use of such an organic solvent in an amount of at least 2.40 parts by weight per part by weight of the methanol.

The term "the solution within the reactor" has the same meaning as above. Since methanol is consumed as the reaction proceeds, the relative amount of the solvent increases as the reaction proceeds. Thus, in the case of a batch type reactor, for example, the solution may be the raw material feed introduced into the reactor. In the case of a continuous flow, stirred tank-type reactor, the solution may be the product continuously discharged from the reactor. In the case of a piston flow type reactor, the solution may be the whole feed, inclusive of recycled solutions, to the reactor.

The methanol carbonylation is performed at a temperature of 140°–250° C., preferably 160°–230° C. and a carbon monoxide partial pressure of 7–30 kg/cm², preferably 10–20 kg/cm², while maintaining the total reaction pressure in the range of 15–60 kg/cm²G, preferably 15–40 kg/cm²G, more preferably 15–30 kg/cm²G. The alkyl iodide, which is preferably methyl iodide, is used in an amount effective to promote the methanol carbonylation, generally in an amount of 1–40% by weight, preferably 5–30% by weight, based on the weight of the solution within the reactor. The rhodium loaded catalyst is used in a catalytically effective amount, generally in an amount of at least 50 ppm by weight, preferably at least 300 ppm by weight, more preferably at least 400 ppm by weight, in terms of elemental rhodium, based on the weight of the solution within the reactor.

BRIEF DESCRIPTION OF DRAWINGS

The present invention will now be described in more detail below with reference to the accompanying drawings, in which.

Figure 1:
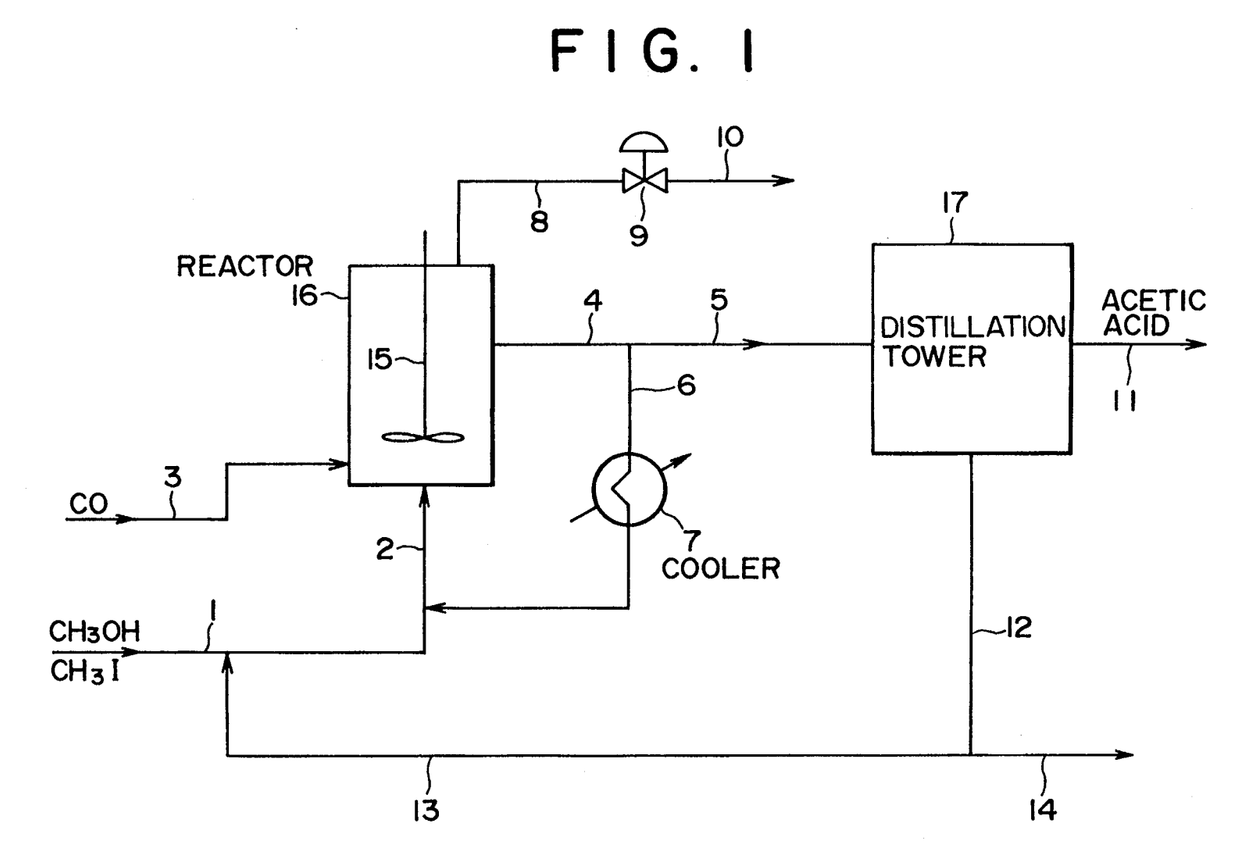
FIGS. 1 and 2 are flow diagrams each schematically illustrating an apparatus for carrying out the process of the present invention.

Referring to FIG. 1, designated as 16 is a reactor containing a rhodium-loaded catalyst, acetic acid as a solvent and methyl iodide as a promoter. The contents in the reactor 16 are homogeneously mixed with a stirrer 15. To the reactor 16 is continuously fed methanol containing methyl iodide through lines 1 and 2 and, at the same time, carbon monoxide gas is continuously introduced into the reactor 16 through a line 3. The methanol and carbon monoxide are contacted with the catalyst in the reactor 16 to produce acetic acid.

The product solution is continuously discharged from the reactor 16 through a line 4 and a portion thereof is fed, through a line 6, to a cooler 7 where it is cooled by indirect heat exchange with a cooling medium with the other portion thereof being fed to a distillation tower 17 through a line 5. The solution cooled in the cooler 7 is recycled to the reactor 16 to maintain the temperature of the reaction solution within the reactor 16 at a predetermined range. The product solution introduced into the distillation tower 17 is separated into acetic acid which is recovered through a line 11 and a residual liquid. A portion of the residual liquid containing by products, such as water, hydrogen iodide, methyl acetate and dimethyl ether, as well as unreacted methanol, methyl iodide and, if desired, acetic acid is recycled through lines 12, 13 and 2 to the reactor 16 while the other portion thereof is, if necessary, discharged from the reaction system through a line 14.

A gas containing unreacted carbon monoxide and vapors of low boiling point matters such as methyl iodide is withdrawn overhead from the reactor 16 and is passed through a line 8, a flow control valve 9 and a line 10 to a suitable separating device (not shown) to separate the low boiling point matters which may be recycled to the reactor 16, if desired.

The carbonylation degree $C_r$ of the reaction solution within the reactor 16 which is equal to the carbonylation degree $C_p$ of the product solution may be controlled by control of the residence time of the solution within the reactor 16. In lieu of the mechanical stirrer 15, the stirring of the reaction solution may be effected by any suitable method such as by introducing the feed gas and/or liquid as a jet stream. The cooling of the product solution for controlling the reaction solution may be effected by any other suitable means such as by flushing.

Figure 2:
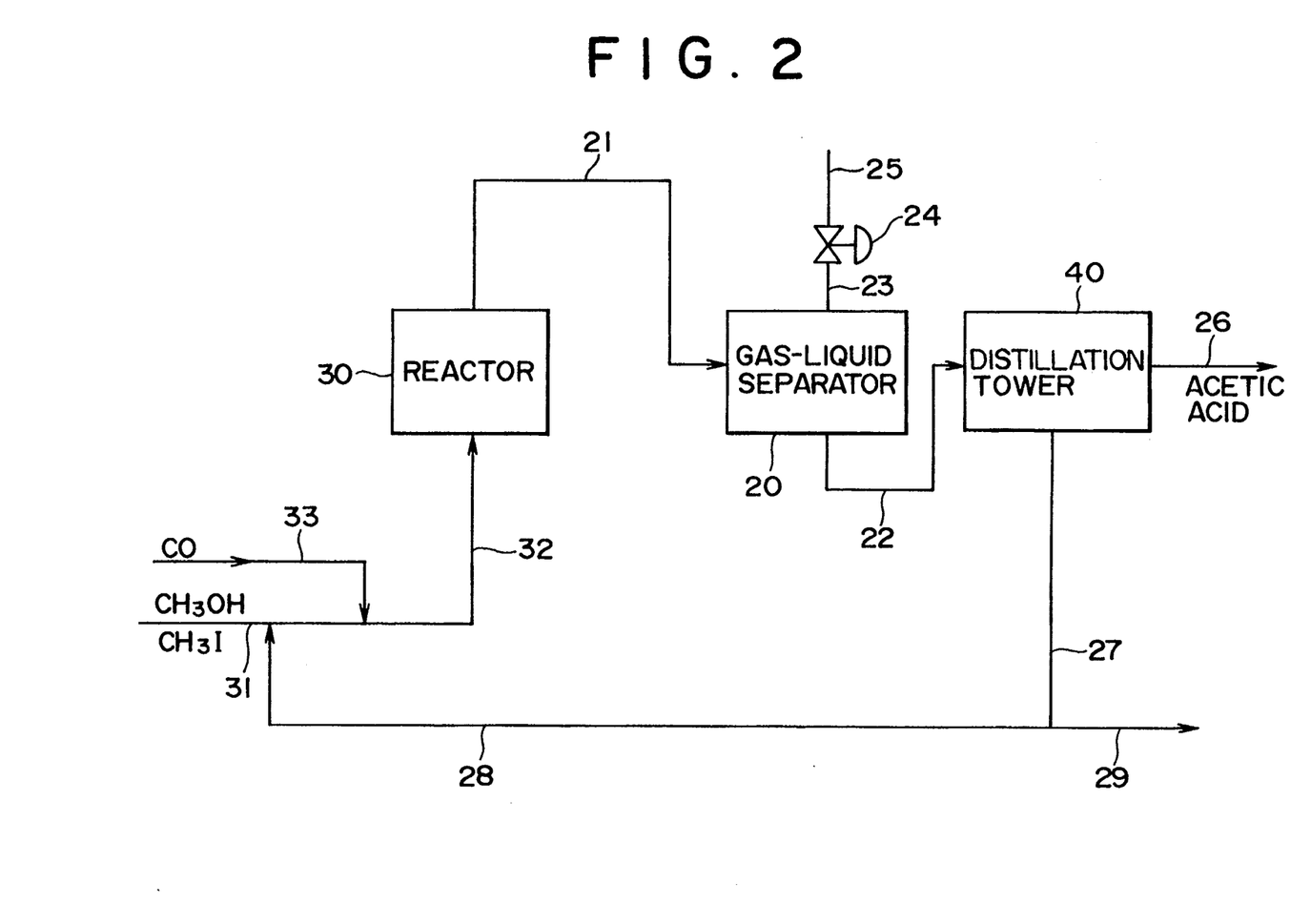

FIG. 2 illustrate a methanol carbonylation system using a piston flow-type reactor 30. The reactor 30 has a plurality of pipes (not shown) connected in parallel with each other and each packed with a rhodium-loaded catalyst. The packed catalyst may be in the form of a fixed bed or an expansible bed. The pipes are surrounded by a sheath into which a cooling medium such as low temperature steam is supplied for indirect heat exchange with the reaction solution flowing within the pipes. The heated steam may be used, for example, as a heat source for a distillation tower 40.

Raw material methanol and methyl iodide are supplied through a line 31 and is introduced, together with carbon monoxide supplied through a line 33 and a solvent-containing recycled solution supplied through a line 28, into an inlet port of the reactor 30 through a line 32, where the liquid/gas feeds are thoroughly mixed with each other. The mixture is then evenly introduced into respective catalyst-containing pipes and is reacted to produce acetic acid.

The reaction mixture is withdrawn from the top of the reactor 30 and is fed to a gas-liquid separator 20 through a line 21, where it is separated into a gas containing unreacted carbon monoxide and a liquid product containing acetic acid. The gas is discharged from the separator 20 and is passed through a line 23, a flow control valve 24 and a line 25 to a suitable separating device (not shown) to separate the low boiling point matters which may be recycled to the reactor 30, if desired. The liquid product separated from the gas is fed through a line 22 to a distillation tower 40 where it is separated into acetic acid which is recovered through a line 26 and a residual liquid which is discharged from the tower 40 though a line 27. A portion of the residual liquid containing by-products, such as water, hydrogen iodide, methyl acetate and dimethyl ether, as well as unreacted methanol, methyl iodide and, if desired, acetic acid is recycled through lines 28 and 32 to the reactor 30 while the other portion thereof is, if necessary, discharged from the reaction system through a line 29.

The following examples will further illustrate the present invention. Percentages and ppm are by weight except otherwise noted.

EXAMPLE 1

A dry, 25% cross-linked poly-4-vinylpyridine/divinyl benzene copolymer resin (Reillex 425 manufactured by Reilly Industries, Inc.) was immersed in methanol, to which were added methyl iodide and acetic acid to obtain a mixture consisting of 6.8 g of the copolymer resin and 140 g of a solution containing 8% methyl iodide, 40% methanol and 52% acetic acid. The mixture was then charged in a 250 cc autoclave equipped with a stirrer together with 0.07 g of $RhCl_3.3H_2O$. After deaeration with carbon monoxide gas, the mixture was heated to 190° C. Then, carbon monoxide was fed to the autoclave through a pressure control valve so that the pressure within the autoclave showed about 40 $kg/cm^2G$ (initial partial pressure of carbon monoxide: 15 $kg/cm^2$). The mixture within the autoclave was reacted at those temperature and pressure for 1 hour. Then the autoclave was cooled to room temperature and was purged with nitrogen gas. The supernatant was removed by decantation and the solids were washed several times with methanol to obtain a rhodium-loaded polymer catalyst having a Rh content of 0.4%. No rhodium was detected in the supernatant upon analysis by the atomic absorption method.

The thus obtained catalyst was mixed with 140 g of a solution consisting of 8% methyl iodide, 40% methanol and 52% acetic acid and the mixture was charged in a 250 cc autoclave equipped with a stirrer. After deaeration with carbon monoxide gas, the mixture ($C_r$: 0.40, $W_f$: 0.0) was heated to 190° C. Then, carbon monoxide was fed to the autoclave through a pressure control valve so that the pressure within the autoclave showed about 40 $kg/cm^2G$ (initial partial pressure of carbon monoxide: 15 $kg/cm^2$), thereby to initiate the reaction. After 180 minutes from the commencement of the reaction, the reaction solution was sampled to analyze the composition thereof. The results of the analysis were as shown in Table 1. The carbonylation degree $C_p$ and the water concentration $W_p$ of the solution were 0.84 and 4.1%, respectively. The solution was found to have a liberated Rh concentration of less than 0.3 ppm. The methanol carbonylation rate was 3.1 mol/liter hour.

EXAMPLE 2

A Rh-loaded catalyst having a Rh content of 0.8% was prepared in the same manner as that in Example 1 except that 10% cross-linked poly-4-vinylpyridine resin (KEX-316 manufactured by Koei Chemical Co., Ltd.) was used in place of Reillex 425 and that the amount of $RhCl_3.3H_2O$ was changed from 0.07 g to 0.14 g. Using this catalyst, methanol carbonylation was performed in the same manner as that in Example 1. After 2 hours reaction, the reaction solution was sampled. The results of analysis are shown in Table 1. The carbonylation degree $C_p$ and the water concentration $W_p$ of the solution were 0.87 and 3.4%, respectively. The solution was found to have a liberated Rh concentration of less than 0.3 ppm. The methanol carbonylation rate was 4.7 mol/liter hour.

EXAMPLE 3

A Rh-loaded catalyst having a Rh content of 0.8% was prepared in the same manner as that in Example 1 except that 20% cross-linked poly-4-vinylpyridine resin (KEX-212 manufactured by Koei Chemical Co., Ltd.) was used in place of Reillex 425 and that the amount of $RhCl_3.3H_2O$ was increased to 0.14 g. Using this catalyst, methanol carbonylation was performed in the same manner as that in Example 2 except that the raw material solution used consisted of 9.5% methyl iodide, 39.5% methanol and 51% acetic acid. After 3 hours reaction, the reaction solution was sampled. The results of analysis are shown in Table 1. The carbonylation degree $C_p$ and the water concentration $W_p$ of the solution were 0.94 and 1.6%, respectively. The solution was found to have a liberated Rh concentration of less than 0.3 ppm. The methanol carbonylation rate was 3.6 mol/liter hour.

EXAMPLE 4

A Rh-loaded catalyst having a Rh content of 0.8% was prepared in the same manner as that in Example 2 except that 30% cross-linked poly-4-vinylpyridine resin (KEX-501 manufactured by Koei Chemical Co., Ltd.) was used in place of KEX 316. Using this catalyst, methanol carbonylation was performed in the same manner as that in Example 2. After 3 hours reaction, the reaction solution was sampled. The results of analysis are shown in Table 1. The carbonylation degree $C_p$ and the water concentration $W_p$ of the solution were 0.91 and 2.3%, respectively. The solution was found to have a liberated Rh concentration of less than 0.3 ppm. The methanol carbonylation rate was 3.4 mol/liter hour.

EXAMPLE 5

The catalyst once used in Example 1 was washed with methanol. Using this catalyst, methanol carbonylation was performed in the same manner as that in Example 1 except that the raw material solution used consisted of 8.0% methyl iodide, 16% methanol and 76% acetic acid ($C_r$: 0.70, $W_f$: 0.0) and the reaction temperature was lowered to 175° C. After 150 minutes reaction, the reaction solution was sampled. The results of analysis are shown in Table 1. The carbonylation degree $C_p$ and the water concentration $W_p$ of the solution were 0.94 and 1.6%, respectively. The solution was found to have a liberated Rh concentration of less than 0.3 ppm. The methanol carbonylation rate was 2.0 mol/liter hour.

EXAMPLE 6

Example 5 was repeated in the same manner as described except that the reaction temperature was raised to 205° C. The results of analysis are shown in Table 1. The carbonylation degree $C_p$ and the water concentration $W_p$ of the solution were 0.94 and 1.4%, respectively. The solution was found to have a liberated Rh concentration of less than 0.3 ppm. The methanol carbonylation rate was 3.3 mol/liter hour.

EXAMPLE 7

A Rh-loaded catalyst having a Rh content of 2.0% was prepared in the same manner as that in Example 1 except that the amount of $RhCl_3.3H_2O$ was increased to 0.70 g. In this case, only about half of the rhodium used was loaded on the polymer.

The thus obtained catalyst was mixed with 140 g of a solution consisting of 8% methyl iodide, 16% methanol and 76% acetic acid and the mixture was charged in a 250 cc autoclave equipped with a stirrer. After deaeration with carbon monoxide gas, the mixture ($C_r$: 0.70, $W_f$: 0.0) was heated to 190° C. Then, carbon monoxide was fed to the autoclave through a pressure control valve so that the pressure within the autoclave showed about 30 kg/cm$^2$G (initial partial pressure of carbon monoxide: 15 kg/cm$^2$), thereby to initiate the reaction. After 50 minutes from the commencement of the reaction, the reaction solution was sampled to analyze the composition thereof. The results of the analysis were as shown in Table 1. The carbonylation degree $C_p$ and the water concentration $W_p$ of the solution were 0.95 and 1.1%, respectively. The solution was found to have a liberated Rh concentration of less than 0.3 ppm. The methanol carbonylation rate was 5.1 mol/liter hour.

EXAMPLE 8

A Rh-loaded catalyst having a Rh content of 5.0% was prepared in the same manner as that in Example 7. Using this catalyst, methanol carbonylation was performed in the same manner as that in Example 7. After 30 minutes reaction, the reaction solution was sampled. The results of analysis are shown in Table 1. The carbonylation degree $C_p$ and the water concentration $W_p$ of the solution were 0.95 and 1.2%, respectively. The solution was found to have a liberated Rh concentration of less than 0.3 ppm. The methanol carbonylation rate was 9.4 mol/liter hour.

EXAMPLE 9

A Rh-loaded catalyst having a Rh content of 0.8% was prepared in the same manner as that in Example 1 except that the amount of $RhCl_3.3H_2O$ was changed from 0.07 g to 0.14 g. Using this catalyst, methanol carbonylation was performed in the same manner as that in Example 7 except that the amount of the raw material solution was reduced from 140 g to 70 g. After 35 minutes reaction, the reaction solution was sampled. The results of analysis are shown in Table 1. The carbonylation degree $C_p$ and the water concentration $W_p$ of the solution were 0.95 and 1.1%, respectively. The solution was found to have a liberated Rh concentration of less than 0.3 ppm. The methanol carbonylation rate was 7.8 mol/liter hour.

EXAMPLE 10

The catalyst once used in Example 7 was washed with methanol. Using this catalyst, methanol carbonylation was performed in the same manner as that in Example 1 except that the raw material solution used consisted of 9.1% methyl iodide, 12.1% methanol, 45.8% acetic acid, 13.1% methyl acetate and 9.9% water ($C_r$: 0.60, $W_f$: 0.14). After 90 and 180 minutes reaction, the reaction solution was sampled. The results of analysis are shown in Table 1. The carbonylation degree $C_p$ and the water concentration $W_p$ of the solution after 90 minutes reaction were 0.94 and 3.9%, respectively, while the carbonylation degree $C_p$ and the water concentration $W_p$ of the solution after 180 minutes reaction were 0.98 and 2.7%. The two solutions were found to have a liberated Rh concentration of less than 0.3 ppm. The methanol carbonylation rates at the 90 minutes reaction and the 180 minutes reaction were 3.7 and 3.2 mol/liter hour, respectively.

COMPARATIVE EXAMPLE 1

A rhodium-loaded catalyst was prepared in the same manner as that in Example 1 except that a 2% cross-linked vinylpyridine polymer (Reillex 402 manufactured by Reilly Industries, Inc.) was used. Methanol carbonylation was performed using this catalyst in the same manner as that in Example 1. However, after 180 minutes reaction, the carbonylation degree $C_p$ of the product was 0.40 (equal to $C_r$). Further, the catalyst was ruptured and turned into a tar-like matter.

COMPARATIVE EXAMPLE 2

Example 1 was repeated in the same manner as described except that the pressure in the autoclave was maintained at about 29 kg/cm$^2$G (initial carbon monoxide partial pressure: 4 kg/cm$^2$). After 200 minutes reaction, the reaction solution was sampled. The results of analysis are shown in Table 1. The carbonylation degree $C_p$ and the water concentration $W_p$ of the solution were 0.48 and 12.8%, respectively. The solution was found to have a liberated Rh concentration of 2.6 ppm. The methanol carbonylation rate was 0.5 mol/liter hour.

COMPARATIVE EXAMPLE 3

Example 1 was repeated in the same manner as described except that the pressure in the autoclave was maintained at about 65 kg/cm$^2$G (initial carbon monoxide partial pressure: 40 kg/cm$^2$). After 200 minutes reaction, the reaction solution was sampled. The results of analysis are shown in Table 1. The carbonylation degree $C_p$ and the water concentration $W_p$ of the solution were 0.88 and 3.2%, respectively. The solution was found to have a liberated Rh concentration of less than 0.3 ppm. The methanol carbonylation rate was 2.9 mol/liter hour. Thus, no additional advantages were obtained by the use of a high pressure as compared with the results of Example 1.

COMPARATIVE EXAMPLE 4

Using the catalyst similar to that of Example 9, methanol carbonylation was performed in the same manner as that in Example 1 except that the raw material solution used consisted of 7.6% methyl iodide, 32% methanol, 45% acetic acid and 16% water ($C_r$: 0.40, $W_f$: 0.51) and that the pressure within the autoclave was maintained at about 40 kg/cm$^2$G (initial carbon monoxide partial pressure: 19 kg/cm$^2$). After 120 minutes reaction, the reaction solution was sampled. The results of analysis are shown in Table 1. The carbonylation degree $C_p$ and the water concentration $W_p$ of the solution were 0.89 and 14.9%, respectively. The solution was found to have a liberated Rh concentration of 4.5 ppm. The methanol carbonylation rate was 4.4 mol/liter hour.

COMPARATIVE EXAMPLE 5

Using the catalyst similar to that of Example 9, methanol carbonylation was performed in the same manner as that in Example 1 except that the raw material solution used consisted of 7.5% methyl iodide, 74.5% methanol, 11.9% acetic acid and 12.2% water ($C_r$: 0.05, $W_f$: 0.27) and that the pressure within the autoclave was maintained at about 50 kg/cm$^2$G (initial carbon monoxide partial pressure: 16 kg/cm$^2$). After 60 minutes reaction, the reaction solution was sampled. The results of analysis are shown in Table 1. The carbonylation degree $C_p$ of the solution were 0.05. The methanol carbonylation rate was 0.9 mol/liter hour.

EXAMPLE 11

Using the catalyst similar to that of Example 9, methanol carbonylation was performed in the same manner as that in Example 1. The reaction solution was occasionally sampled after 50, 80, 140 and 240 minutes from the start of the reaction. The water concentration $W_p$ of the product solution was found to change in the order of 9.9%, 8.5%, 1.8% and 0.2% as the reaction proceeded. The methanol carbonylation rate was constantly 4.5 mol/liter hour till 140 minutes. The reaction solution showed carbonylation degree $C_p$ of 0.93 in the case of the 140 minutes reaction and 0.98 in the case of the 240 minutes reaction. The methanol carbonylation rate was 0.3 mol/liter hour after 240 minutes from the start of the reaction. The average carbonylation rate was 2.3 mol/liter hour. Each of the sampled solutions had a liberated Rh content of less than 0.3 ppm.

EXAMPLE 12

A catalyst (5.8 g on dry basis) similar to that of Example 9 was placed in an autoclave together with acetic acid and methyl iodide. With stirring, methanol carbonylation was performed while continuously feeding raw materials and continuously discharging a portion of the reaction solution so as to maintain the amount of the reaction solution within the autoclave at 120 ml. The reaction was continuously performed at 190° C. under 30 kg/cm$^2$G for 100 hours. The raw material feed includes 18N liter/hour of carbon monoxide, 15 g/hour of methanol and 2 g/hour of methyl iodide ($W_f$: 0.0). The product solution continuously discharged from the autoclave consisted of 0.1% dimethyl ether, 8.3% methyl iodide, 0.4% methanol, 63.2% acetic acid, 22.4% methyl acetate and 5.6% water ($W_p$=5.6%), as shown in Table 1. The carbonylation degree $C_p$ ($=C_r$) was 0.81. The liberated Rh concentration in the product solution was found to be less than 0.3 ppm.

EXAMPLE 13

The raw material feed in the reaction in Example 12 was changed to 13.2N liter/hour of carbon monoxide, 22 g/hour of methanol and 95 g/hour of acetic acid and 13 g/hour of methyl iodide ($W_f$: 0.0) after the reaction in Example 12 had been continued for 100 hours. Then, with this new feed, the reaction was further continued for another 100 hours under the same conditions as those in Example 12. The carbonylation degree $C_p$ ($=C_r$) was 0.87. The liberated Rh concentration in the product solution was found to be less than 0.3 ppm. The composition of the product solution was as shown in Table 1.

TABLE 1

| Example No. | $C_p$ | Composition of Product Solution (%) | | | | | |
|---|---|---|---|---|---|---|---|
| | | Dimethyl Ether | Methyl Iodide | Methanol | Acetic Acid | Methyl Acetate | Water |
| 1 | 0.84 | 0.5 | 5.0 | 1.0 | 73.3 | 16.1 | 4.1 |
| 2 | 0.87 | 0.1 | 6.1 | 0.8 | 75.6 | 13.9 | 3.4 |
| 3 | 0.94 | 0.0 | 6.8 | 0.1 | 85.2 | 6.3 | 1.6 |
| 4 | 0.91 | 0.1 | 6.3 | 0.1 | 80.6 | 10.4 | 2.3 |
| 5 | 0.94 | 0.0 | 7.0 | 0.1 | 85.0 | 6.3 | 1.6 |
| 6 | 0.94 | 0.0 | 6.9 | 0.0 | 85.3 | 6.4 | 1.4 |
| 7 | 0.95 | 0.0 | 5.9 | 0.1 | 87.1 | 5.8 | 1.1 |
| 8 | 0.95 | 0.0 | 5.0 | 0.0 | 87.9 | 5.9 | 1.2 |
| 9 | 0.95 | 0.0 | 5.4 | 0.1 | 87.7 | 5.8 | 1.0 |
| 10 | 0.94 | 0.1 | 7.5 | 0.1 | 82.3 | 4.4 | 3.9 |
| | 0.98 | 0.1 | 6.2 | 0.7 | 90.4 | 0.0 | 2.7 |
| 11 | 0.93 | 0.0 | 7.0 | 0.1 | 84.5 | 6.7 | 1.7 |
| 12 | 0.81 | 0.1 | 8.3 | 0.4 | 63.2 | 22.4 | 5.6 |
| 13 | 0.87 | 0.1 | 7.0 | 0.0 | 74.1 | 15.1 | 3.7 |

TABLE 1-continued

| Example No. | $C_p$ | Composition of Product Solution (%) | | | | | |
|---|---|---|---|---|---|---|---|
| | | Dimethyl Ether | Methyl Iodide | Methanol | Acetic Acid | Methyl Acetate | Water |
| C.4* | 0.89 | 1.0 | 6.0 | 1.0 | 71.0 | 6.1 | 14.9 |

*Comparative Example 4

EXAMPLE 14

A Rh-loaded catalyst having a Rh content of 0.6% was prepared in the same manner as that in Example 1 except that the amount of RhCl$_3$.3H$_2$O was changed from 0.07 g to 0.05 g. The thus obtained catalyst was mixed with 140 g of a solution consisting of 8% methyl iodide, 70% methanol and 22% acetic acid (acetic acid/methanol weight ratio: 0.31) and the mixture was charged in a 250 cc autoclave equipped with a stirrer. After deaeration with carbon monoxide gas, the mixture was heated to 190° C. Then, carbon monoxide was fed to the autoclave through a pressure control valve so that the pressure within the autoclave showed about 50 kg/cm$^2$G (initial partial pressure of carbon monoxide: 15 kg/cm$^2$), thereby to initiate the reaction. After 120 minutes from the commencement of the reaction, the reaction solution was sampled to determine the methanol carbonylation rate from the amount of carbon monoxide consumed. The rate was revealed to be 3.0 mol/liter hour. Since the vapor pressure of the reaction solution was reduced as the reaction proceeded, the carbon monoxide partial pressure increased to 20 kg/cm$^2$ after the 120 minutes reaction.

EXAMPLE 15

A catalyst similar to that used in Example 14 was mixed with 140 g of a solution consisting of 8% methyl iodide, 51% methanol and 41% acetic acid (acetic acid/methanol weight ratio: 0.78) and the mixture was charged in a 250 cc autoclave equipped with a stirrer. After deaeration with carbon monoxide gas, the mixture was heated to 190° C. Then, carbon monoxide was fed to the autoclave through a pressure control valve so that the pressure within the autoclave showed about 45 kg/cm$^2$G (initial partial pressure of carbon monoxide: 15 kg/cm$^2$), thereby to initiate the reaction. After 120 minutes from the commencement of the reaction, the reaction solution was sampled to determine the methanol carbonylation rate from the amount of carbon monoxide consumed. The rate was revealed to be 3.6 mol/liter hour. The carbon monoxide partial pressure increased to 20 kg/cm$^2$ after the 120 minutes reaction.

EXAMPLE 16

A catalyst similar to that used in Example 14 was mixed with 140 g of a solution consisting of 8% methyl iodide, 41% methanol and 51% acetic acid (acetic acid/methanol weight ratio: 1.2) and the mixture was charged in a 250 cc autoclave equipped with a stirrer. After deaeration with carbon monoxide gas, the mixture was heated to 190° C. Then, carbon monoxide was fed to the autoclave through a pressure control valve so that the pressure within the autoclave showed about 40 kg/cm$^2$G (initial partial pressure of carbon monoxide: 15 kg/cm$^2$), thereby to initiate the reaction. After 120 minutes from the commencement of the reaction, the reaction solution was sampled to determine the methanol carbonylation rate from the amount of carbon monoxide consumed. The rate was revealed to be 3.6 mol/liter hour. The carbon monoxide partial pressure increased to 20 kg/cm$^2$ after the 120 minutes reaction.

EXAMPLE 17

A catalyst similar to that used in Example 14 was mixed with 140 g of a solution consisting of 8% methyl iodide, 24% methanol and 68% acetic acid (acetic acid/methanol weight ratio: 2.8) and the mixture was charged in a 250 cc autoclave equipped with a stirrer. After deaeration with carbon monoxide gas, the mixture was heated to 190° C. Then, carbon monoxide was fed to the autoclave through a pressure control valve so that the pressure within the autoclave showed about 40 kg/cm$^2$G (initial partial pressure of carbon monoxide: 28 kg/cm$^2$), thereby to initiate the reaction. After 60 minutes from the commencement of the reaction, the reaction solution was sampled to determine the methanol carbonylation rate from the amount of carbon monoxide consumed. The rate was revealed to be 3.7 mol/liter hour. The carbon monoxide partial pressure increased to 30 kg/cm$^2$ after the 60 minutes reaction.

EXAMPLE 18

Example 17 was repeated in the same manner as described except that the pressure within the autoclave was adjusted to 40 kg/cm$^2$G (initial carbon monoxide partial pressure: 18 kg/cm$^2$). The reaction solution was sampled after 60, 120 and 180 minutes from the commencement of the reaction. The carbonylation rate was 3.7 mol/liter hour at 60 and 120 minutes reaction stages. The average rate up to the 180 minutes reaction was 1.8 mol/liter hour. The carbon monoxide partial pressure increased to 20, 22 and 24 kg/cm$^2$ after 60, 120 and 180 minutes, respectively. The composition of each product solution is shown in Table 2.

EXAMPLE 19

Example 17 was repeated in the same manner as described except that the pressure within the autoclave was adjusted to 20 kg/cm$^2$G (initial carbon monoxide partial pressure: 8 kg/cm$^2$). The reaction solution was sampled after 60 minutes from the commencement of the reaction. The carbonylation rate was 2.5 mol/liter hour. The carbon monoxide partial pressure increased to 10 kg/cm$^2$ after the 60 minutes reaction.

EXAMPLE 20

A catalyst similar to that used in Example 14 was mixed with 140 g of a solution consisting of 8% methyl iodide, 31% methanol, 45% acetic acid (acetic acid/methanol weight ratio: 1.45) and 16% water and the mixture was charged in a 250 cc autoclave equipped with a stirrer. After deaeration with carbon monoxide gas, the mixture was heated to 190° C. Then, carbon monoxide was fed to the autoclave through a pressure control valve so that the pressure within the autoclave showed about 40 kg/cm$^2$G (initial partial pressure of carbon monoxide: 19 kg/cm$^2$), thereby to initiate the reaction. After 120 and 150 minutes from the commencement of the reaction, the reaction solution was sampled to determine the methanol carbonylation rate from the amount of carbon monoxide consumed. The rate was revealed to be 3.8 mol/liter hour at 120 and 150 minutes reaction stages. The carbon monoxide partial pressure increased to 30 kg/cm² after the 150 minutes reaction.

EXAMPLE 21

A catalyst similar to that used in Example 14 was mixed with 140 g of a solution consisting of 9% methyl iodide, 12% methanol, 45% acetic acid, 23% methyl acetate ((acetic acid + methyl acetate)/methanol weight ratio: 5.67) and 10% water and the mixture was charged in a 250 cc autoclave equipped with a stirrer. After deaeration with carbon monoxide gas, the mixture was heated to 190° C. Then, carbon monoxide was fed to the autoclave through a pressure control valve so that the pressure within the autoclave showed about 40 kg/cm²G (initial partial pressure of carbon monoxide: 11 kg/cm²), thereby to initiate the reaction. After 60 minutes from the commencement of the reaction, the reaction solution was sampled to determine the methanol carbonylation rate from the amount of carbon monoxide consumed. The rate was revealed to be 3.7 mol/liter hour. The carbon monoxide partial pressure increased to 30 kg/cm² after the 60 minutes reaction. The composition of the product solution is shown in Table 2.

TABLE 2

| Example No. | Reaction Time | Composition of Product Solution (%) | | | | | |
|---|---|---|---|---|---|---|---|
| | | Dimethyl Ether | Methyl Iodide | Methanol | Acetic Acid | Methyl Acetate | Water |
| 14 | 1 | 0.0 | 6.5 | 0.9 | 75.5 | 13.8 | 3.4 |
|    | 2 | 0.1 | 6.8 | 0.2 | 85.0 | 6.3 | 1.6 |
|    | 3 | 0.0 | 6.2 | 0.1 | 92.2 | 1.1 | 0.4 |
| 16 | 2 | 1.0 | 6.0 | 1.0 | 71.0 | 6.1 | 14.9 |
|    | 2.5 | 0.0 | 2.9 | 0.1 | 84.1 | 0.0 | 12.9 |
| 17 | 1 | 0.4 | 8.0 | 2.0 | 63.0 | 18.0 | 8.0 |

COMPARATIVE EXAMPLE 6

A catalyst similar to that used in Example 14 was mixed with 140 g of a solution consisting of 10% methyl iodide and 90% methanol and the mixture was reacted in the same manner as that in Example 14 except that the pressure within the autoclave was adjusted to about 70 kg/cm²G (initial partial pressure of carbon monoxide: 35 kg/cm²). After 120 minutes from the commencement of the reaction, the reaction solution was sampled to determine the methanol carbonylation rate from the amount of carbon monoxide consumed. The rate was revealed to be 0.1 mol/liter hour. The carbon monoxide partial pressure decreased to 15 kg/cm² after the 120 minutes reaction.

COMPARATIVE EXAMPLE 7

A catalyst similar to that used in Example 14 was mixed with 140 g of a solution consisting of 8% methyl iodide, 84% methanol and 8% acetic acid (acetic acid/methanol weight ratio: 0.1) and the mixture was reacted in the same manner as that in Example 14 except that the pressure within the autoclave was adjusted to about 50 kg/cm²G (initial partial pressure of carbon monoxide: 15 kg/cm²). After 120 minutes from the commencement of the reaction, the reaction solution was sampled to determine the methanol carbonylation rate from the amount of carbon monoxide consumed. The rate was revealed to be 0.7 mol/liter hour. The carbon monoxide partial pressure was increased to 20 kg/cm² after the 120 minutes reaction.

We claim:

1. A process for the production of acetic acid, comprising:

reacting an alkyl iodide with a pyridine-containing resin to quaternize the pyridine component of said resin;

reacting carbon monoxide, an alkyl iodide and a rhodium salt to form a rhodium carbonyl complex which ionically binds to the quaternized resin to form a solid catalyst;

introducing a feed including methanol, carbon monoxide, an alkyl iodide and a solvent into a reaction zone containing said solid catalyst;

contacting said feed with said solid catalyst to react said methanol with carbon monoxide and to obtain a reaction solution; and discharging at least a portion of said reaction solution from said reaction zone to obtain a product solution;

wherein said solvent includes at least one organic solvent selected from the group consisting of carboxylic acids having at least two carbon atoms and carboxylic acid esters having at least two carbon atoms, and wherein said reaction is performed at a temperature of 140°–250° C. and a pressure of 15–60 kg/cm²G with a partial pressure of carbon monoxide of 7–30 kg/cm² while maintaining (a) the water concentration of said product solution in the range of 0.5–10% by weight and (b) the carbonylation degree $C_r$ of the solution within said reaction zone at 0.15 or more, wherein the carbonylation degree $C_r$ is given by the following equation:

$$C_r = (M[CH_3COOH] + M[CH_3COOCH_3] + M[CH_3COOR^1])/(M[CH_3COOH] + 2M[CH_3COOCH_3] + 2M[CH_3OCH_3] + M[CH_3COOR^1] + M[R^3COOCH_3] + M[CH_3OR^3] + M[CH_3OH])$$

wherein $M[CH_3COOH]$, $M[CH_3COOCH_3]$, $M[CH_3COOR^1]$, $M[CH_3OCH_3]$, $M[R^2COOCH_3]$, $M[CH_3OR^3]$ and $M[CH_3OH]$ represent the amounts, in terms of molarity, of $CH_3COOH$, $CH_3COOCH_3$, $CH_3COOR^1$ where $R^1$ represents an alkyl group having at least two carbon atoms, $CH_3OCH_3$, $R^2COOCH_3$ where $R^2$ represents an alkyl group having at least two carbon atoms, $CH_3OR^3$ where $R^3$ represents an alkyl group having at least two carbon atoms and $CH_3OH$, respectively, which are present in the solution within said reaction zone.

2. A process as claimed in claim 1, wherein the solution within said reaction zone contains carbonyl group-containing compounds having at least two carbon atoms in an amount of at least 0.30 part by weight per part by weight of the methanol present in the solution within said reaction zone.

3. A process as claimed in claim 1, wherein said reaction is performed while maintaining the following conditions (c)–(e): (c) the water concentration of said product solution being 1–5% by weight, (d) the carbonylation degree $C_p$ of said product solution being at least 0.80, and (e) the water content $W_f$ of said feed being 0.30 or less, said carbonylation degree $C_p$ and said water content $W_f$ being given by the following equations:

$$C_p = (M[CH_3COOH] + M[CH_3COOCH_3] + M[CH_3COOR^1])/(M[CH_3COOH] + 2M[CH_3COOCH_3] + 2M[CH_3OCH_3] + M[CH_3COOR^1] + M[R^2COOCH_3] + M[CH_3OR^3] + M[CH_3OH])$$

wherein $M[CH_3COOH]$, $M[CH_3COOCH_3]$, $M[CH_3COOR^1]$, $M[CH_3OCH_3]$, $M[R^2COOCH_3]$, $M[CH_3OR^3]$ and $M[CH_3OH]$ represent the amounts, in terms of molarity, of $CH_3COOH$, $CH_3COOCH_3$, $CH_3COOR^1$ where $R^1$ represents an alkyl group having at least two carbon atoms, $CH_3OCH_3$, $R^2COOCH_3$ where $R^2$ represents an alkyl group having at least two carbon atoms, $CH_3OR^3$ where $R^3$ represents an alkyl group having at least two carbon atoms and $CH_3OH$, respectively, which are present in said product solution, and $$W_f = (M[H_2O] - M[CH_3COOCH_3] - M[CH_3COOR^1] - M[R^2COOCH_3] - M[CH_3OCH_3] - M[CH_3OR^3] - M[R^4OR^5])/(M[CH_3COOH] + 2M[CH_3COOCH_3] + 2M[CH_3OCH_3] + M[CH_3COOR^1] + M[R^2COOCH_3] + M[CH_3OR^3] + M[CH_3OH])$$

wherein $M[H_2O]$, $M[CH_3COOCH_3]$, $M[CH_3COOR^1]$, $M[R^2COOCH_3]$, $M[CH_3OCH_3]$, $M[CH_3OR^3]$, $M[R^4OR^5]$) and $M[CH_3OH]$ represent the amounts, in terms of molarity, of $H_2O$, $CH_3COOCH_3$, $CH_3COOR^1$, $R^2COOCH_3$, $CH_3OCH_3$, $CH_3OR^3$, $R^4OR^5$ and $CH_3OH$ which are present in said feed.

4. A process as claimed in claim 1, wherein said alkyl iodide is methyl iodide.

5. A process as claimed in claim 1, wherein said solid catalyst is used in an amount of at least 400 ppm by weight in terms of elemental rhodium based on the weight of the solution within said reaction zone.

6. A process for the production of acetic acid, comprising:

reacting an alkyl iodide with a pyridine-containing resin to quaternize the pyridine component of said resin;

reacting carbon monoxide, an alkyl iodide and a rhodium salt to form a rhodium carbonyl complex which ionically binds to the quaternized resin to form a solid catalyst;

reacting, in a reaction zone, carbon monoxide with methanol in a solvent at a temperature of 140°–250° C. in the presence of an alkyl iodide and said solid catalyst;

wherein said solvent includes an organic solvent selected from the group consisting of solvents having at least two carbonyl groups and mixtures thereof, wherein said reaction is performed at a pressure of 15–60 kg/cm²G with a partial pressure of carbon monoxide of 7–30 kg/cm², and wherein the solution within said reaction zone contains said organic solvent in an amount of at least 0.30 part by weight per part by weight of the methanol contained therein.

7. A process as claimed in claim 6, wherein said alkyl iodide is methyl iodide and said organic solvent includes at least one member selected from the group consisting of acetic acid and methyl acetate.

8. A process as claimed in claim 6, wherein said solid catalyst is used in an amount of at least 400 ppm by weight in terms of elemental rhodium based on the weight of the solution within said reaction zone.

* * * * *

UNITED STATES PATENT AND TRADEMARK OFFICE
CERTIFICATE OF CORRECTION

PATENT NO. : 5,334,755
DATED : August 2, 1994
INVENTOR(S) : YONEDA et al

It is certified that error appears in the above-indentified patent and that said Letters Patent is hereby corrected as shown below:

Col. 7, line 17, "$W_f$ofthe" should read --$W_f$ of the--.

Col. 18, line 51, "$M[R^3$" should read --$M[R^2$--.

Signed and Sealed this

Twenty-fifth Day of April, 1995

Attest:

BRUCE LEHMAN

*Attesting Officer*  *Commissioner of Patents and Trademarks*